United States Patent [19]

Dart et al.

[11] 4,110,184

[45] Aug. 29, 1978

[54] PHOTOCURABLE DENTAL FILLING COMPOSITIONS

[75] Inventors: Edward Charles Dart; John Burnett Cantwell; James Rodney Traynor; Joseph Franciszek Jaworzyn; Jozef Nemcek, all of Runcorn, England

[73] Assignee: Imperial Chemical Industries Limited, London, England

[21] Appl. No.: 514,289

[22] Filed: Oct. 11, 1974

Related U.S. Application Data

[63] Continuation-in-part of Ser. No. 463,145, Apr. 22, 1974, abandoned.

[30] Foreign Application Priority Data

Apr. 24, 1973 [GB] United Kingdom ............... 19270/73

[51] Int. Cl.$^2$ ............................ C08F 2/46; C08F 4/00
[52] U.S. Cl. ............................ 204/159.23; 96/115 P; 204/159.16; 204/159.18; 204/159.24; 260/42.18; 260/42.22; 260/42.53; 260/42.15; 260/859 R; 260/998.11; 528/48; 528/76; 528/80; 528/85
[58] Field of Search .................. 204/159.15, 159.16, 204/159.19, 159.23, 159.24; 260/77.5, 859

[56] References Cited

U.S. PATENT DOCUMENTS

| | | | |
|---|---|---|---|
| 3,297,745 | 1/1967 | Fekete et al. | 260/471 |
| 3,509,234 | 4/1970 | Burlant et al. | 260/859 |
| 3,625,744 | 12/1971 | Juna et al. | 117/93.31 |
| 3,664,861 | 5/1972 | Okamura et al. | 117/93.31 |
| 3,709,866 | 1/1973 | Waller | 260/27 R |
| 3,759,807 | 9/1973 | Osborn et al. | 204/159.23 |
| 3,759,809 | 9/1973 | Carlick et al. | 204/159.23 |
| 3,772,404 | 11/1973 | Knight et al. | 260/859 R |
| 3,825,479 | 7/1974 | Carlick et al. | 204/159.23 |
| 3,840,448 | 10/1974 | Osborn et al. | 204/159.23 |
| 3,876,518 | 4/1975 | Borden et al. | 204/159.14 |
| 3,878,077 | 4/1975 | Borden et al. | 204/159.16 |

FOREIGN PATENT DOCUMENTS

7,214,074 4/1973 Netherlands.
1,408,265 10/1975 United Kingdom.

*Primary Examiner*—Richard B. Turer
*Attorney, Agent, or Firm*—Cushman, Darby & Cushman

[57] ABSTRACT

A dental filling composition comprising (a) from 60 to 80% by weight of the composition of an inorganic particulate filler selected from glass, quartz or silica of which at least 50% of the particles have a maximum dimension of not greater than 300 microns, and (b) a polymerizable material comprising:
a polymerizable prepolymer being the reaction product of a urethane prepolymer and 2-hydroxy-ethyl methacrylate;
the said urethane prepolymer being the reaction product of a di-isocyanate selected from the group consisting of 4,4'-di-isocyanatodiphenylmethane, hexamethylene di-isocyanate, 4,4'-dicyclohexylmethane di-isocyanate and 2,4-tolylene di-isocyanate, and a diol being the condensate obtained by reacting 2,2-bis-(p-hydroxyphenyl)propane and propylene oxide in a molar ratio of 1:2;
up to 100% by weight of the polymerizable prepolymer of methacrylic acid or an ester of methacrylic acid selected from the group consisting of methyl methacrylate, ethylene glycol dimethacrylate, hydroxyethyl methacrylate, triethylene glycol dimethacrylate and allyl methacrylate;
and from 0.01 to 10% by weight of the polymerizable material of a photosensitive catalyst comprising a photosensitizer selected from the group consisting of fluorenone, benzil, camphorquinone and α-naphthil, and a reducing agent being dimethylaminoethyl methacrylate.

1 Claim, No Drawings

PHOTOCURABLE DENTAL FILLING COMPOSITIONS

This invention relates to photocurable dental compositions and is a continuation-in-part of application Ser. No. 463,145, filed April 22, 1974, now abandoned Dental compositions useful in the production of, for example, dental fillings, have been proposed which comprise an ethylenically unsaturated polymerisable material, a suitable particulate filler, and a photosensitive catalyst capable of initiating polymerisation of the material on irradiation of the composition with ultraviolet radiation of a suitable wavelength. Polymerisation of the meterial results in cure of the composition. Photosensitive catalysts which have been proposed for use in the compositions include, for example, benzoin alkyl ethers.

We now provide a dental composition which includes a photosensitive catalyst which enables the composition to be cured rapidly on irradiation with ultraviolet radiation or with visible radiation, or with a mixture of ultraviolet and visible radiation. Furthermore, as the novel photosensitive catalysts generally enable the dental compositions to be cured on irradiation with visible radiation only it is possible, with the compositions of the present invention, to avoid using the ultraviolet radiation which may be harmful to the patient, for example, if directed towards the patient's eye.

Where the particulate filler in the composition is capable of absorbing ultraviolet radiation then ultraviolet irradiation of such a composition containing an ultraviolet photosensitive catalyst may not lead to cure of the composition, or at most may lead only to a very slow rate of cure. However, where the composition contains a visible light photosensitive catalyst as in the composition of the present invention then the presence in the composition of the ultraviolet absorbing particulate filler may have at most only a small effect on the rate of cure of the composition on irradiation with visible radiation.

According to the present invention there is provided a dental composition which is a fluid composition comprising a polymerisable prepolymer containing at least two polymerisable ethylenically unsaturated groups and being the reaction product of a urethane prepolymer and an ethylenically unsaturated monomer reactive with the urethane prepolymer, a particulate filler, preferably an inorganic filler, and a photosensitive catalyst comprising (a) at least one photosensitiser selected from fluorenone, substituted derivatives thereof, and α-diketones having the structure

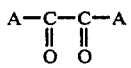

in which the groups A, which may be the same or different, are hydrocarbyl groups or substituted hydrocarbyl groups, and (b) at least one reducing agent capable of reducing the photosensitiser when the photosensitiser is in an excited state.

In the particulate filler, which is preferably inorganic, at least 50% of the particles should have a maximum dimension of not greater than 1000 microns.

By fluid composition we mean a composition which has sufficient mobility that it may be readily moulded at ambient temperature, for example, merely by moulding under hand pressure. Suitably, the composition will have a pastelike consistency.

The dental composition may be applied to the tooth, e.g. as a filling to a cavity in the tooth, and the polymerisable prepolymer may be polymerised so that the composition is formed into a hard material. This polymerisation process will hereinafter be referred to as curing of the composition.

The composition may contain a polymerisable prepolymer which is a solid, and as the filler will also be solid it is often necessary in order to produce a composition which is fluid, to add to the composition sufficient liquid ethylenically unsaturated monomer copolymerisable with the polymerisable prepolymer to make the composition fluid, and in particular to give the composition a paste-like consistency. If desired, the composition may include liquid copolymerisable ethylenically unsaturated monomer even where the polymerisable prepolymer is itself a liquid.

The dental compositions of the present invention may be cured by irradiating the composition with ultraviolet radiation, that is, with radiation having a wavelength in the range about 230 mμ up to 400 mμ. the compositions may also be, and preferably are, cured by irradiating with visible radiation and especially with visible radiation having a wavelength in the range 400 mμ to 500 mμ. Alternatively, a mixture of ultraviolet and visible radiation may be used.

In the α-diketone having the structure

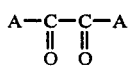

the groups A, when hydrocarbyl, may be, for example, aliphatic, e.g. alkyl having from 1 to 10 carbon atoms; aromatic, e.g. phenyl; cycloaliphatic, e.g. cyclohexyl; aralkyl, e.g. benzyl; or alkaryl, e.g. tolyl. Alternatively, the groups A may together form a divalent radical such that in the photosensitiser the groups A together with the carbonyl groups form a cyclic structure. For example, the groups A may form a divalent aliphatic group, or they may form an aromatic group, and in particular may form a fused aromatic ring system.

Suitable α-diketones include biacetyl having the structure

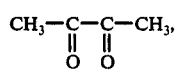

benzil having the structure

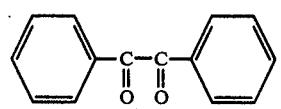

α-naphthil having the structure

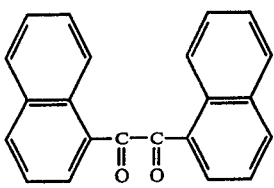

β-naphthil having the structure

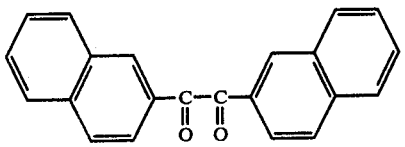

acenaphthacene having the structure

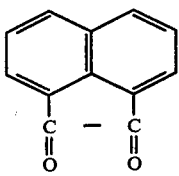

or camphorquinone having the structure

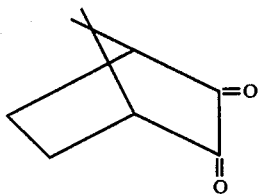

Where the groups A are substituted hydrocarbyl and substituent group or groups should not result in substantial inhibition of polymerisation of the polymerisable material. Examples of photosensitisers in which the groups A are substituted hydrocarbyl include p,p'-dimethoxy benzil and p,p'-dichlorobenzil. Particularly preferred photosensitisers are camphorquinone and benzil.

The photosensitive catalyst may be present in the dental composition in a concentration of, for example, 0.01 to 20% by weight of the polymerisable material in the composition, although concentrations outside this range may be used if desired. The concentration of the photosensitiser may be up to 10% by weight of the polymerisable material. Preferably, the photosensitiser is present in a concentration in the range 0.5 to 5% by weight of the polymerisable material in the composition.

The reducing agent present in the photosensitive catalyst should be capable of reducing the photosensitiser when the photosensitiser is in an excited state. The reducing agent should have little or no inhibiting effect on polymerisation. Whether or not a reducing agent has an inhibiting effect may be determined by means of an simple experiment, for example, by effecting polymerisation of the polymerisable material in the composition by means of a thermal initiator alone, and in the presence of a reducing agent in the desired concentration, and comparing the rates of polymerisation in the presence of and in the absence of the reducing agent.

Suitable reducing agents include compounds having the structure

where M is an element of Group Vb of the Periodic Table of the Elements and the units R, which may be the same or different, are hydrogen atoms, hydrocarbyl groups, substituted hydrocarbyl groups, or groups in which two units R together with the element M form a cyclic ring system, no more than two of the units R being hydrogen atoms and the element M not being attached directly to an aromatic group.

The Periodic Table of the Elements referred to is that published in "Advanced Inorganic Chemistry," second edition, by F. A. Cotton and G. Wilkinson (Interscience 1966).

The element M in the reducing agent may be, for example, phosphorous or more preferably nitrogen. If desired, M may be arsenic or antimony.

The reducing agent may be primary, secondary or tertiary, that is, in the structure

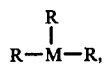

two, one or none of the units R respectively may be hydrogen atoms. For example, the reducing agent may be a primary, secondary or tertiary amine or phosphine.

One or more of the groups R may be hydrocarbyl. The hydrocarbyl group may be alkyl, cycloalkyl or aralkyl. Suitably the group R may be an alkyl group having from 1 to 10 carbon atoms.

Examples of suitable reducing agents in which one or more of the units R is hydrocarbyl include propylamine, butylamine, pentylamine, hexylamine, dimethylamine, diethylamine, dipropylamine, dibutylamine, dipentylamine, trimethylamine, triethylamine, tripropylamine, tributylamine, tripentylamine, dimethylaminoethylmethacrylate, and long chain fatty amines, e.g. $C_{18}H_{37}NMe_2$.

It is to be understood that throughout this specification where we refer to specific examples of suitable reducing agents in which the element M is nitrogen we also wish to include corresponding specific examples in which the element M is phosphorus, arsenic or antimony.

One or more of the units R may be substituted hydrocarbyl groups and in particular the hydrocarbyl group may carry a substituent having the structure

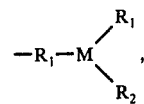

where M is an element of Group Vb of the Periodic Table of the Elements and the unit $R_1$ is, for example, an alkylene chain and the units $R_2$, which may be the same or different, are, for example, hydrogen atoms or hydrocarbyl groups.

Examples of reducing agents having the structure

in which at least one of the units R is a substituted hydrocarbyl group include diamines of the structure

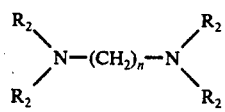

in which n is a whole number of a least two and the groups $R_2$, which may be the same or different are hydrogen atoms or hydrocarbyl, especially alkyl groups. For example, the reducing agent may be ethylene diamine, trimethylene diamine, tetramethylene diamine, pentamethylene diamine or hexamethylene diamine, or N-hydrocarbyl, especially N-alkyl derivatives thereof. Other suitable reducing agents include derivatives having the structure

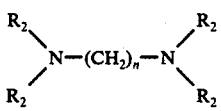

in which one or more of the hydrogen atoms in the $-CH_2$ units carry an

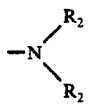

group, especially an $-NH_2$ group.

Examples of reducing agents in which the element M forms part of a cyclic ring system include piperidine, and N- hydrocarbyl, especially N-alkyl, derivatives of piperidine.

Other reducing agents include triallylamine,

allyl thiourea and soluble salts of aromatic sulphinic acids.

Suitably the concentration of the reducing agent may be in the ranges hereinbefore described in respect of the photosensitiser. Preferably, the reducing agent is present in a concentration of 1% to 5% by weight of the polymerisable material in the dental composition.

The polymerisable material in the dental composition is a polymerisable ethylenically unsaturated material. Preferably at least part of the material comprises a material containing a plurality of ethylenically unsaturated groups such that polymerisation of the material results in the production of a cross-linked polymer.

In order that the cured dental composition should possess higher strength and modulus it is preferred that the polymerisable material possesses at least one cyclic group. In the case where the polymerisable material includes a plurality of ethylenically unsaturated groups it is preferred that the material possesses at least one cyclic group in the chain between the ethylenically unsaturated groups.

The urethane prepolymer may be formed by reacting at least one polyisocyanate with at least one polyfunctional compound containing isocyanate-reactive groups, e.g. with a polyol, which may be for example, a polyether or polyester polyol, or with a polycarboxylic acid. The urethane prepolymer may possess isocyanate end groups, in which case the ethylenically unsaturated monomer reactive therewith should possess an isocyanate-reactive group e.g. a hydroxyl or carboxyl group. Alternatively, the urethane prepolymer may possess, for example, hydroxyl or carboxyl end groups where the prepolymer is formed from a polyfunctional compound which is a polyol or a polycarboxylic acid respectively, in which case the ethylenically unsaturated monomer reactive therewith should possess a group reactive with the hydroxyl or carboxyl group, e.g. an isocyanate group. Preferably, the urethane prepolymer possesses isocyanate end groups.

The urethane prepolymer may conveniently have a linear, non-branched structure, that is, it may be formed by reaction of a diisocyanate and a difunctional compound, e.g. a diol or a dicarboxylic acid.

Preferably, for reasons of convenience and in particular for reasons of ease of preparation the urethane prepolymer may be linear, may carry isocyanate end groups, and may be formed by reaction of a diol with a diisocyanate to yield a urethane prepolymer having the structure

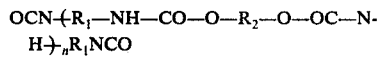

where the diisocyanate has the structure $OCN-R_1-NCO$ and the diol has the structure $HO-R_2-OH$, $R_1$ and $R_2$ being divalent hydrocarbyl groups, n being an integer.

in this case reaction of the urethane prepolymer with the ethylenically unsaturated monomer reactive therewith will yield a polymerisable prepolymer having the structure

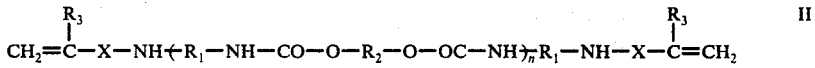

where X is a divalent radical and $R_3$ is hydrogen or a hydrocarbyl group.

In order that the urethane prepolymer may have isocyanate end-groups it will be appreciated that a molar excess of the diisocyanate over the diol must be used in the preparation of the prepolymer, the value of n in the prepolymer depending on the molar proportion of diisocyanate to diol used, the value of n decreasing as this latter ratio increases.

Formation of the isocyanate-ended prepolymer may be assisted by the use of catalysts known in the art to assist polyurethane formation, for example, tertiary amines, and metal salts, e.g. stannous octoate and in particular dibutyl tin dilaurate.

The reaction of the diol and diisocyanate may produce a viscous urethane prepolymer and, especially where n is a large number, the prepolymer may be solid, and thus it is desirable in these circumstances that the reaction of the diol and the diisocyanate be effected in the presence of an inert diluent. Similarly, where the urethane prepolymer is very viscous or solid reaction of the latter prepolymer with ethylenically unsaturated monomer containing an isocyanate-reactive group to form the polymerisable prepolymer may desirably be effected in the presence of an inert diluent. The diluent should be substantially free of groups which are reactive with isocyanate groups, at least to such an extent that the diluent does not interfere with the formation of the prepolymer. The diluent could be the liquid ethylenically unsaturated monomer copolymerisable with the prepolymer.

Where the polymerisable prepolymer having the structure II is prepared in an inert diluent, the prepolymer may be separated from the diluent, e.g. by evaporation of the diluent or by addition to the diluent of a non-solvent for the polymerisable prepolymer.

In order that the filling prepared by curing of the dental filling composition should possess a higher strength and modulus and a higher resistance to creep, it is preferred that the urethane prepolymer be formed from a polyisocyanate and a polyfunctional compound at least one of which, and preferably both of which, possesses at least one cyclic group, preferably an aromatic group, in the chain between the isocyanate-reactive groups in the polyfunctional compound or between the isocyanate groups in the polyisocyanate respectively. Thus, where the urethane prepolymer is formed from a diol and a diisocyanate having the respective structures HO—R$_2$—OH and OCN—R$_1$—NCO it is preferred that at least one of the divalent hydrocarbyl radicals R$_1$ and R$_2$ has an in-chain cyclic group, preferably an aromatic group.

Where a dental filling having a particularly high strength and modulus and resistance to creep is desired it is preferred that the polymerisable prepolymer in the dental filling composition have the structure II in which R$_1$, R$_2$, R$_3$ and X have the designations previously ascribed, n is a whole number of from 1 to 20, at least one of the groups R$_1$ and R$_2$ containing at least one cyclic group in the chain of the prepolymer, there being not more than 30 atoms, and where higher strength is desired, not more than 20 and preferably not more than 12 atoms in the chain between adjacent cyclic groups, and when n is one and only R$_2$ contains at least one cyclic group in the chain there are not more than 30, preferably not more than 20, and more preferably not more than 12 atoms in the chain between the cyclic group in R$_2$ and the nitrogen atom attached to the group X.

For reasons of ease of preparation of the urethane prepolymer, and consequently the polymerisable prepolymer, the value of n in the urethane prepolymer is preferably not greater than 10 and is more preferably not greater than 5, that is, the molar ratio of isocyanate groups in the diisocyanate or mixture thereof to hydroxyl groups in the diol or mixture thereof from which the isocyanate-ended prepolymer is produced is preferably 1.1:1 or greater, and more preferably 1.2:1 or greater.

Most suitably, the value of n in the urethane prepolymer is not greater than 3, that is, the molar ratio of isocyanate groups in the diisocyanate or mixture thereof to hydroxyl groups in the diol or mixture thereof from which the urethaneprepolymer is produced is suitably 1.33:1 or greater.

Examples of diols containing cyclic groups which may be used in the preparation of the urethane prepolymer include, for example, cycloalkane diols, e.g. 1:3- and 1:4-cyclohexane diol and a diol having the structure

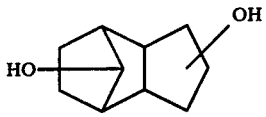

in which case the group R$_2$ in the urethane prepolymer has the structure

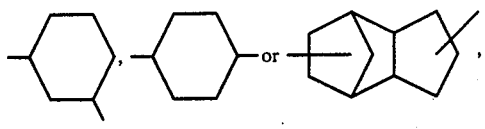

respectively. Other suitable diols include, for example, cycloalkane dialkanols, e.g. cyclohexane dimethanol or cyclohexane diethanol; polycycloalkane diols, polycycloalkane dialkanols, aryl dialkanols and condensates of alkylene oxides with aromatic compounds containing two phenolic groups.

Particularly preferred diols on account of the desirable properties of the fillings which may be produced are diols of the structure

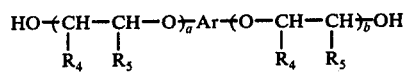

that is, oxyalkylated derivatives of phenolic compounds, where R$_4$ and R$_5$ are hydrogen atoms or alkyl groups, e.g. methyl, and Ar is a divalent aromatic group in which each free valency is on an aromatic carbon atom, and in which $a + b$ together preferably total not more than 8 and $a$ is preferably not greater than $b + 3$.

In this case the divalent group R$_2$ has the structure

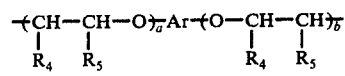

Ar may be mononuclear, e.g. as in phenylene, fused polynuclear as in naphthalene or anthracene, or preferably has the structure

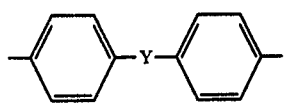

in which Y is a divalent link, e.g. —O—, —SO$_2$—, —CO— or —CH$_2$ or substituted derivative of —CH$_2$ e.g.

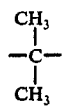

Suitably, one of the groups R$_4$ and R$_5$ is hydrogen and the other is methyl, or both R$_4$ and R$_5$ are hydrogen, that is, the diol may be prepared by reaction of propylene oxide or ethylene oxide with a phenolic compound having the structure HO — Ar — OH, preferably

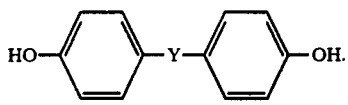

Preferably a plus b is not greater than 4.

Examples of diols which do not have cyclic groups in the chain include, for example, ethylene glycol and propylene glycol, in which case $R_2$ has the structure —$CH_2$—$CH_2$ or

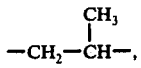

butylene glycol, diethylene glycol and derivatives thereof in which one or more of the carbon atoms are substituted by atoms or groups which are unreactive towards hydroxyl and isocyanate group.

Diisocyanates containing cyclic groups which may be used to prepare the urethane prepolymer include, for example, diisocyanates in which the chain between the free valencies is provided with at least one aromatic group or at least one cycloaliphatic group, or in which the chain between the free valencies includes in combination at least one aromatic and at least one cycloaliphatic group.

Cycloaliphatic diisocyanates include for example, diisocyanates of the structure:

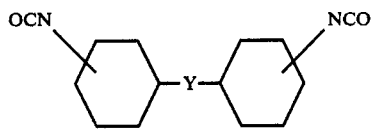

where —Y— is a divalent link which may be, for example, —$CH_2$— or substituted derivative thereof, —O—, —$SO_2$—, —CO—, and the isocyanate groups are linked meta or para to the groups Y. A particular example is 4:4′-dicyclohexylmethane diisocyanate.

Aromatic diisocyanates which may be used include, for example, 2:4- or 2:6-tolylene diisocyanates, or mixtures thereof, in which case the divalent group $R_1$ has the structure

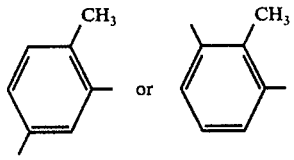

or a combination of said structures. Another suitable aromatic diisocyanate is that having the structure

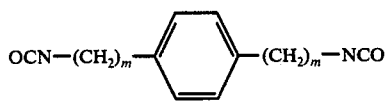

where m is a whole number chosen such that there are preferably not more than 30 atoms between cyclic groups in the urethane prepolymer derived therefrom. A suitable diisocyanate having the latter structure is xylylene diisocyanate.

A particularly suitable diisocyanate is that having the structure:

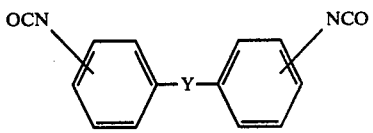

where Y is a divalent link which may have the designations hereinbefore described and in which the isocyanate groups are linked meta or para to the group Y. A preferred example is 4:4′-diisocyanatodiphenyl methane.

Diisocyanates which do not contain cyclic groups may be used in the production of the urethane prepolymer. Suitable such diisocyanates include, for example, tetramethylene diisocyanate, pentamethylene diisocyanate and hexamethylene diisocyanate, in which case the divalent group $R_1$ will have the structure —$(CH_2)_4$—, —$(CH_2)_5$— or $(CH_2)_6$—.

The ethylenically unsaturated monomer which is reacted with the urethane prepolymer to produce the polymerisable prepolymer may have, for example, an isocyanate group or an isocyanate-reactive group depending on whether the urethane prepolymer possesses respectively, isocyanate groups or isocyanate-reactive groups.

The ethylenically unsaturated monomer reacted with the urethane prepolymer to produce the polymerisable prepolymer may be, for example, acrylic acid or a derivative thereof having the structure

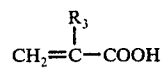

where $R_3$ is hydrogen or a hydrocarbyl group, for example, alkyl, e.g. methyl. In this case the group —X— in the polymerisable prepolymer II has the structure

after elimination of carbon dioxide from the initially formed product of reaction.

Other suitable ethylenically unsaturated monomers include, for example, hydroxyl containing monomers having the structure:

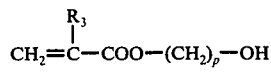

where $R_3$ is hydrogen or a hydrocarbyl group, for example, alkyl, e.g. methyl, and p is a whole number of at least 2, and is preferably 2, or derivatives of said monomer in which one or more of the hydrogen atoms in the group —$(CH_2)_p$— are substituted by a hydrocarbyl group, for example, alkyl, e.g. methyl. In this case the group -X- in the polymerisable prepolymer II has the structure —COO—$(CH_2)_p$—O—CO—.

Suitable examples include hydroxy ethyl or hydroxy propyl acrylate or methacrylate made by reaction of acrylic acid or methacrylic acid with ethylene oxide or propylene oxide, in which case the group X in the polymerisable prepolymer II will have the structure

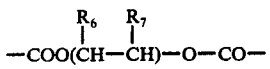

in which, respectively, both $R_6$ and $R_7$ are hydrogen, and one of $R_6$ and $R_7$ is hydrogen and the other is methyl.

Other suitable isocyanate-reactive ethylenically unsaturated monomers include allyl alcohol, in which case the group X in the polymerisable prepolymer has the structure $-CH_2-O-CO-$, and acrylamide and methacrylamide, in which case the group X in the polymerisable prepolymer II has the structure $-CONH-OCO-$.

As stated hereinbefore at least 50% of the particles in the filler should have a maximum dimension of not greater than 1000 microns. By this we mean that the maximum dimension of the particles in any direction should not be greater than 1000 microns. Thus, where the filler is in the form of spheres at least 50% of the spheres should have a diameter of not greater than 1000 microns. Where the filler is in the form of fibres at least 50% of the fibres should have a length of not greater than 1000 microns. Preferably substantially all of the particles in the filler have a maximum dimension of not greater than 1000 microns.

Mixing of the filler with the polymerisable prepolymer generally becomes easier with decrease in the size of the particles in the filler. The preferred maximum dimension of the particles in the filler is determined by the shape of the filler. Thus, where the filler is in the form of fibres the maximum dimension of the fibres is preferably not greater than 500 microns, more preferably not greater than 100 microns. On the other hand, where the filler is in the form of spheres, platelets or is irregularly shaped the maximum dimension of the particles in the filler is preferably not greater than 300 microns and is more preferably in the range 1 to 100 microns.

In order that a hard dental filling may be produced by curing of the composition it is desirable that the particles of filler have a Knoop hardness of at least 100. In general, the greater the hardness of particles of filler in the composition the greater the hardness of the dental filling produced by curing of the composition and for this reason it is preferred that the Knoop hardness of the filler be at least 300, and more preferably at least 500. In general, the required hardness, and in particular the preferred hardness, is possessed by inorganic fillers.

In order that the dental filling produced by curing of the dental filling composition may have the appearance of a natural tooth it is preferred to use a filler which is translucent.

The dental filling composition may contain, for example, between 10 and 90% of filler by weight of the composition, although in order that the dental filling produced by curing of the composition should have a particularly desirable abrasion resistance, hardness, low shrinkage on curing and low coefficient of thermal expansion, the dental filling compositions preferably contains between 30 and 80%, and more preferably between 60 and 80% of filler by weight of the dental filling composition. Mixtures of different fillers may be used.

The filler may, for example, be in the form of spheres, platelets, fibres, whiskers or it may be irregularly shaped. Suitable fillers include, for example, apatite, soda glass, quartz, silica gel, borosilicate glass, synthetic sapphire (alumina) or metal fibres.

Mixing of the polymerisable prepolymer with the filler to form the dental filling composition may be effected by stirring together the prepolymer and filler. However, as the polymerisable prepolymer, optionally together with a copolymerisable monomer, may be viscous and thus difficult to stir with the filler so as to achieve adequate mixing the polymerisable prepolymer, optionally together with copolymerisable monomer, may conveniently be diluted with a suitable diluent so as to reduce the viscosity thus enabling adequate mixing of the filler to be more readily achieved. When mixing has been effected the diluent may be removed, e.g. by evaporation. Suitably, the diluent may be a copolymerisable ethylenically unsaturated monomer, the monomer, if desired, being removed completely after mixing has been achieved, or where the dental filling composition is to contain copolymerisable ethylenically unsaturated monomer, the level of the monomer subsequently being reduced to the desired extent.

In order that a dental filling may be produced in which the filler adheres particularly well to the cured polymerisable prepolymer in the filling it is much preferred that the filler be treated with a coupling agent which is capable of reacting with both the filler and the polymerisable prepolymer before mixing of the filler and polymerisable prepolymer is effected. The coupling agent should have the effect of increasing the strength of the bond between the filler and the cured polymerisable prepolymer in the filling.

Suitable coupling agents for use with glass include silanes, e.g. γ-methacryloxypropyltrimethoxysilane, γ-aminopropyltriethoxysilane and γ-glycidoxypropyltrimethoxysilane.

As stated hereinbefore, the dental filling composition may contain liquid ethylenically unsaturated monomer copolymerisable with the polymerisable prepolymer, and should contain such a monomer when the polymerisable prepolymer is a solid in order that the dental filling composition be fluid and in particular have a plaste-like consistency.

The amount of such ethylenically unsaturated monomer used may desirably be just sufficient to achieve the desired fluidity in the dental filling composition. As the use of such a monomer may lead to a reduction in the strength of the filling made from the composition it is preferred to use in the filling composition not more than 100% of ethylenically unsaturated monomer by weight of polymerisable prepolymer, and more preferably not more than 50% by weight.

Suitable liquid copolymerisable ethylenically unsaturated monomers, the polymers of which should be water insoluble, include vinyl monomers, e.g. vinyl esters and acrylic and methacrylic acids. The monomers should be non toxic.

Suitable vinyl esters include, for example, vinyl acetate, esters of acrylic acid having the formula $CH_2=CH-COOR_6$, where $R_6$ is an alkyl, aryl, alkaryl, aralkyl or cycloalkyl group. For example $R_6$ may be an alkyl group having from 1 to 20, and preferably 1 to 10 carbon atoms. Particular vinyl esters which may be mentioned include for example, methyl acrylate, ethyl acrylate, n- and iso-propyl acrylates, and n-, iso- and tertiary-butyl acrylates.

Other suitable vinyl esters include, for example, esters of formula $CH_2 = C(R_7)COOR_6$, where $R_7$ may be an alkyl, e.g. a methyl group. In the ester of formula $CH_2$ = $C(R_7)COOR_6$, $R_6$ and $R_7$ may be the same or different. Particular vinyl esters which may be mentioned include, for example, methyl methacrylate, ethyl methacrylate, n- and iso-propyl methacrylate, and n- iso- and tertiary-butyl methacrylate.

Mixtures of acids and esters may be used.

Polyfunctional vinyl monomers, that is, monomers containing two or more vinyl groups are also suitable. Suitable monomers include, for example, glycol dimethacrylate, diallyl phthalate, and triallyl cyanurate.

The dental filling composition of the present invention may be moulded into the desired shape of the dental filling and then may be cured to form a hard filling by polymerising the polymerisable prepolymer, optionally together with an ethylenically unsaturated monomer copolymerisable therewith.

Curing of the compositon to produce a dental filling is assisted by a photosensitive catalyst. It is desirable that the catalyst be capable of curing the composition at relatively low temperature, e.g. at or near ambient temperature, as the use of elevated temperatures may lead to discomfort to the patient being treated.

The invention is now illustrated by the following Examples in which all parts are expressed as parts by weight.

EXAMPLE 1

352 Parts of a condensate obtained by reacting 2:2-bis(p-hydroxyphenyl)propane and propylene oxide in a molar ratio of 1:2 were heated to melt the condensate and stirred under reduced pressure to degas the condensate.

500 Parts of 4:4'-diisocyanatodiphenyl methane were similarly heated, stirred and degassed separately. The condensate and the diisocyanate (molar proporton of diisocyanate:condensate 2:1) were then mixed together and 556 parts of methyl methacrylate which had been dried over calcium hydride were added to the mixture followed by 0.14 part of dibutyl tin dilaurate. The mixture was cooled by means of ice-bath to control the exotherm produced by the urethane prepolymer formation reaction so that the temperature did not rise above 55° C. Stirring was continued for 1½ hours after the end of the exotherm.

260 Parts of 2-(hydroxyethyl)methacrylate, which had previously been distilled and degassed were then added and the resultant mixture was stirred for 1½ hours to form the ethylenically unsaturated polymerisable prepolymer.

60 Parts of the mixture of polymerisable prepolymer and methyl methacrylate prepared above were mixed with 180 parts of glass spheres, (Ballatini 3000 CPOl, Plastichem Ltd) 80% by weight of the spheres having a diameter between 4 and 44 microns.

The mixture was then stirred, further methyl methacrylate was added to aid mixing, and there was then added 6 parts of a catalyst solution formed by dissolving 2 parts of benzil in 4 parts of dimethylaminoethyl methacrylate and 4 parts of methyl methacrylate. After stirring for 15 minutes the pressure was reduced and the methyl methacrylate which had been added to aid stirring was removed by evaporation.

The paste-like mixture was then drawn into a cylindrical glass mould and exposed to radiation from a blue lamp for 15 minutes to cure the mixture.

The cured material had the following properties.

| | |
|---|---|
| Compressive strength | 178 N mm$^{-2}$ |
| Compressive modulus | 3690 N mm$^{-2}$ |
| Rockwell Hardness | 171 Scale H |
| Flexural Modulus | 14500 N mm$^{-2}$ |
| Water absorption (after 65 days immersion in water at 37° C). | 0.75 wt. % |

EXAMPLE 2

The procedure of Example 1 was followed except that 30 parts of the mixture of ethylenically unsaturated polymerisable prepolymer and methyl methacrylate and 3 parts of the catalyst solution were used, and in place of the glass spheres, there was used 60 parts of hammer milled glass fibres having a dimension of 10 microns × 200 microns (Glass Fibres Ltd). Before mixing with the other components of the composition the glass fibres were surface coated with γ-methacryloxypropyltrimethoxysilane by adding 100 parts of glass fibre, which had previously been heated to 400° C and allowed to cool in a dessicator, to a solution of 1 part of γ-methacryloxypropyltrimethoxysilane in 100 parts of methanol, stirring for 1 hour, evaporating the methanol, screening the fibres through a 62 micron mesh, and finally heating the fibres to 140° C to cure the silane.

The cured material had the following properties.

| | |
|---|---|
| Compressive strength | 201 N mm$^{-2}$ |
| Compressive modulus | 3640 N mm$^{-2}$ |
| Rockwell Hardness | 82 Scale B |
| Rockwell Hardness | 168 Scale H |
| Abrasion resistance | 0.05 mg mm$^{-2}$ |

EXAMPLE 3

The procedure of Example 1 was followed except that 15 parts of the mixture of ethylenically unsaturated polymerisable prepolymer and methyl methacrylate and 1.5 parts of the catalyst were used, and in place of the glass spheres, there was used 36 parts of quartz powder the surface of which had been coated with γ-methacryloxypropyltrimethoxysilane following the procedure described in Example 2.

The cured material had the following properties.

| | |
|---|---|
| Compressive strength | 157.6 N mm$^{-2}$ |
| Compressive modulus | 3050 N mm$^{-2}$ |
| Rockwell Hardness | 81 Scale B |
| Rockwell Hardness | 170 Scale H |
| Abrasion resistance | 0.007 mg mm$^{-2}$ |
| Coefficient of linear thermal expansion. | 33.7 ppm at 40° C |

EXAMPLE 4

500 g. of freshly-distilled 4,4'-diisocyanatodiphenyl methane were washed with 300 ml of methylene chloride into a 5 liter flanged necked flask which had been purged with nitrogen gas. The flask was then fitted with a glass anchor stirrer, nitrogen purge, water condenser and thermometer.

352 g. of a molten condensate obtained by condensing 2,2-bis(p-hydroxydiphenol)propane and propylene oxide, and 0.15 g. of dibutyl tin dilaurate were weighed into a 1 liter dropping funnel which had been purged with nitrogen gas. 200 ml of methylene chloride were added to the dropping funnel to prevent the condensate from solidifying.

The dropping funnel was then placed above the flask and its contents were added dropwise to the flask over a period of 45 minutes after which the reaction was allowed to proceed for approx. 45 minutes at which time 300 g. of hydroxyethyl methacrylate were added together with 0.15 g. of dibutyl tin dilaurate over a period of 3 minutes. There was a rise in temperature of the contents of the flask and when this had subsided the flask was heated on a water bath (refluxing methylene chloride) and its contents stirred under a nitrogen purge until the infra red spectrum of the resulting product showed only a trace of isocyanate groups to be present (about 3 days).

The water bath was then removed and methanol was added to the stirred contents of the flask to cause separation of the polymerisable polymer therein. The contents of the flask were allowed to settle and then the methanol layer was syphoned off and discarded. Washing with methanol as above was repeated several times until a clear methanol layer was obtained. The polymerisable prepolymer in the flask was then dried at room temperature under vacuum until a dry foam resulted. The foam was then crushed and dried to remove traces of methanol.

In the absence of blue light, 13.37 parts of the polymerisable prepolymer powder were dissolved in 10.94 parts of ethylene glycol dimethacrylate and 0.625 part of dimethylaminoethyl methacrylate were added to the solution, followed by 0.0625 part of camphorquinone. 75 Parts of a borosilicate glass powder of particle size less than 53 microns and coated with 1% by weight of γ-methacryloxypropyl trimethoxy silane were stirred into the mixture and the resulting fluid paste was passed through a roll mill during which passage it was degassed.

cylindrical samples of the paste of diameter 3 mm. and length 2.5 mm in polytetrafluoroethylene moulds were irradiated with light using a light source fitted with an 18 inch fibre optic, for 2 minutes. The cured samples were removed from the moulds and stored under water at 37° C and tested after periods of 1 hour, 24 hours and 1 week. The results are shown in the Table below.

TABLE

| Time | Av. compressive strength (N mm$^{-2}$) | Av. Tensile strength (N mm$^{-2}$) | Rockwell Hardness (Scale H) |
|---|---|---|---|
| 1 hour | 259 | 42 | — |
| 24 hours | 274 | 45 | 115 |
| 1 week | 301 | 46 | — |

EXAMPLE 5

2.585 Parts of a polymerisable prepolymer prepared as in Example 4 were dissolved in 2.115 parts of ethylene glycol dimethacrylate and 0.1 part of fluorenone and 0.2 part of dimethylaminoethyl methacrylate were added to the solution. 7.5 parts of borosilicate glass powder (as in Example 4 but coated with 2% by weight of the silane) were mixed into the resin with de-gassing and then thick samples of the resulting paste were cured as in Example 4 for 100 minutes using as light source a low-intensity mercury lamp filtered to transmit radiation of 437 microns. The depth of cure was 1.5 mms.

EXAMPLE 6

A paste was prepared and cured as in Example 5 except that α-naphthil was employed instead of fluorenone. The depth of cure was 2.5 mm.

EXAMPLES 7-12

6.7 Parts of the polymerisable prepolymer prepared as in Example 4 were dissolved in 3.3 parts of methyl methacrylate and 0.2 parts of a solution of fluorenone (0.1 part) in dimethylaminoethyl methacrylate (4 parts) were added to the solution. 15 Parts of filler were stirred in, and the resulting paste was drawn into a glass tube of diameter 6 mm. The samples then were cured by irradiation with light from a fluorescent tube for 30 minutes. The cured samples were cut into 12 mm lengths and their compressive strengths determined.

| Example No. | Filler | Compressive Strength (N mm$^{-2}$) |
|---|---|---|
| 7 | Borosilicate glass (below 53 microns) | 178 |
| 8 | Glass platelets (1/32" diam.) | 98 |
| 9 | Ballotini glass beads | 158 |
| 10 | Quartz (below 53 microns) | 158 |
| 11 | Silica gel spheres (below 53 microns) | 120 |
| 12 | Hammer-milled glass fibres (soda glass - 10 microns diam. 200 microns length). | 202 |

EXAMPLE 13

5.5 Parts of the polymerisable prepolymer as in Example 4 were dissolved in 4.5 parts of ethylene glycol dimethacrylate and 0.025 parts of N,N-dimethyl p-toluidine were added to the solution.

0.3 Part of the mixture was mixed for a few seconds with 0.7 part of a coated filler, using a spatula. The coated filler was a coated borosilicate glass powder of particle size less than 53 microns and was obtained by coating 23.33 g. of powdered glass successively with 0.23 part of γ-methacryloxypropyl trimethoxy silane and 0.03 part of benzoyl peroxide from methylene chloride.

The resulting paste was packed into 3 mm × 3 m cylindrical moulds which were allowed to stand for several hours after which the rigid samples were removed and tested. The rigid material had a compressive strength of 160 N mm$^{-2}$ and a diametrical compression of 30 N mm$^{-2}$.

EXAMPLE 14

33.33 Parts of a polymerisable prepolymer prepared as in Example 1 were dissolved in 16.66 parts of methyl methacrylate and 170 parts of Ballotini glass beads (FPO1 3000) of av. diam. 4.4 microns were mixed into the solution. 5 Parts of a solution of dimethylaminoethyl methacrylate (40%) and benzil (20%) in methyl methacrylate (40%) were added and the mixture heated. Excess methyl methacrylate was added and then the mixture was stirred for 15 minutes after which excess methyl methacrylate was removed under vacuum.

The resulting paste was packed in 3 conical cavities drilled in the canine teeth of a Beagle bitch and cured in situ using an 18 inch fibre optics light guide. After 26 months the fillings have remained in the teeth and have showed no visible signs of major mechanical failures or of working loose in the cavities.

EXAMPLES 15–22

A polymerisable prepolymer was prepared as described in Example 4. In the absence of blue light, 3.1 g. of the prepolymer were dissolved in 2.54 g. of monomer (see below) and 0.24 g. of dimethylaminoethylmethacrylate was added to the solution followed by 0.12 g. of benzil. 14 g. of powdered borosilicate glass of particle size less than 53 microns and coated with 2% by weight of γ-methacryloxypropyl trimethoxy silane was stirred into the mixture (an amount such that the filler was 70% by weight of the composition) and the resulting paste was passed through a roll mill during which it was de-gassed.

Cylindrical samples of the paste of diameter 3 mm and length 2½ mm were cured in polytetrafluoroethylene moulds by irradiation for 1 hour at a distance of 12 inches from a Thorn sealed beam lamp. The samples were removed from the moulds after 1 hour and tested for compressive strength, and hardness.

| Example No. | Monomer |
|---|---|
| 15 | methyl methacrylate |
| 16 | methacrylic acid |
| 17 | hydroxyethyl methacrylate |
| 18 | vinyl toluene |
| 19 | styrene |
| 20 | triethylene glycol dimethacrylate |
| 21 | ethylene glycol dimethacrylate |
| 22 | allyl methacrylate |

| Example No. | Compressive Strength (N/mm$^{-2}$) | Rockwell Hardness (Scale H) |
|---|---|---|
| 15 | 173 | 56 |
| 16 | 172 | 54 |
| 17 | 164 | 48 |
| 18 | 166 | 30 |
| 19 | 163 | 22 |
| 20 | 179 | 70 |
| 21 | 184 | 85 |
| 22 | 155 | 52 |

EXAMPLE 23

A. The procedure of Example 21 was repeated except that after exposure of the sample to radiation for 1 hour the sample was removed from the mould and allowed to stand for 2 days prior to testing.

B. For purposes of comparison the above procedure was repeated using a different polymerisable prepolymer. The prepolymer was prepared as follows:

Freshly distilled 2,4-toluene diisocyanate was washed into a flask with methylene chloride and a mixture of 2,2-propane bis[3-(4-phenoxy)-1,2-hydroxy propane-1-methacrylate] and dibutyl tin dilaurate was added dropwise to the flask. The reaction was allowed to proceed until infra-red analysis of the mixture indicated that only a trace of isocyanate groups was present. Methanol was added to the flask to cause separation of the resulting prepolymer which was then dried and finally crushed.

C. Again for purposes of comparison the procedure of A. was repeated using a prepolymer prepared as in B. except that phenyl isocyanate was used instead of 2,4-toluene diisocyanate.

D. For further purposes of comparison, procedure A. was repeated using a prepolymer prepared as in B. but using anisidene diisocyanate instead of 2,4-toluene diisocyanate.

E. In still further comparison, procedure A. was again repeated using a prepolymer prepared as in B. but using 4,4'-diisocyanato diphenyl methane instead of 2,4-toluene diisocyanate.

|  | Compressive Strength (N mm$^{-2}$) | Tensile Strength (N mm$^{-2}$) | Rockwell Hardness (Scale H) | Depth of cure (mins) after 1000 secs |
|---|---|---|---|---|
| A | 197 | 37 | 105 | 4.7 |
| B | 178 | 32 | 88 | — |
| C | 149 | 28 | sample shattered | — |
| D* | — | — | — | — |
| E | 201 | 34 | 96 | 3.1 |

*The material showed very poor cure properties and testable samples were not obtained.

EXAMPLE 24

A. 35.2 g. (0.1 mole) of oxypropylated Bisphenol A were dissolved in approx. 100g. of methylene chloride and the resulting solution was added dropwise to a solution of 33.6 g. (0.2 mole) of hexamethylene diisocyanate in 100 g. of methylene chloride under an atmosphere of nitrogen gas. 4 drops of dibutyl tin dialurate (available under the trade name "Mellite 12") were added as catalyst. The mixture was stirred under nitrogen for 1 hour after which it was heated under reflux conditions for 9 hours. The mixture was then cooled and a solution of 26 g. (0.2 mole) of 2-hydroxyethyl methacrylate in 100 g. of methylene chloride was added, after which the mixture was heated under reflux conditions for 3 hours. The mixture was then cooled and the resulting polymerisable prepolymer was isolated as a viscous gum by treatment of the mixture with petroleum ether followed by removal of residual solvent in a rotary evaporator.

A dental filling composition was prepared from the viscous gum to the formulation:

| | |
|---|---|
| Viscous gum | 13.37 g. |
| ethylene glycol dimethacrylate | 10.94 g. |
| camphorquinone | 0.0625 g. |
| dimethylaminoethylmethacrylate | 0.625 g. |
| *borosilicate glass powder (<53 microns diameter) | 75 g. |

*treated with 1% by weight of silane (A174) coupling agent.

In preparing the composition, the ethylene glycol dimethacrylate was weighed into a 250 ml. beaker containing the viscous gum. The mixture was stirred until the gum had dissolved and then the amine and the camphorquinone were added with stirring. When the catalyst had completely dissolved, the glass powder filler was stirred into the composition to produce a paste which then was placed in a vacuum chamber in which it was degassed for approx. 2 minutes.

Samples of the degassed composition were charged to a polytetrafluorethylene mould of length 3 mm and diameter 3 mm, and the samples then were exposed for 2 minutes to radiation from a standard* lamp and 18 inch long fibre optics, after which time they were immersed in water for 24 hours at 37° C and then tested. The following properties were determined:

| | | |
|---|---|---|
| Compressive Strength | average | 323.4 N mm$^{-2}$ |
|  | maximum | 341.0 N mm$^{-2}$ |
| Tensile Strength (diametral) | average | 55.4 N mm$^{-2}$ |
|  | maximum | 59.4 N mm$^{-2}$ |

-continued

| Depth of Cure (after 1 minute) | 6 mm |

A 150w/21v G.e. quartz line lamp

B. For the purposes of comparison the above procedure was repeated but using 4.4'-diisocyanatodiphenyl methane diisocyanate (0.2 mole) instead of hexamethylene diisocyanate.

C–G. For purposes of comparison, samples 3 mm × 3 mm of conventional dental filling materials were prepared in the normal way and tested.

C. Prestige dental filling composition (Lee Pharmaceuticals)
D. Cosmic dental filling composition (De Trey)
E. HL-72 dental filling composition (Lee Pharmaceuticals)
F. Conventional amalgam
G. Encapsulated conventional amalgam

| Property | A | B | C | D | E | F | G |
|---|---|---|---|---|---|---|---|
| Compressive Strength (average)(N mm$^{-2}$) | 323.4 | 260 | 298 | 267 | 253 | 266 | 350 |
| Tensile Strength (average)(N mm$^{-2}$) | 55.4 | 46.0 | 45.0 | 48.0 | 41.0 | 43.0 | 49.0 |
| Depth of Cure after 1 minute (mms) | 6 | 3 | — | — | — | — | — |

The handling properties of compositions A and B were also compared. The polymerisable prepolymer in compositon A is a viscous gum whilst that in composition B is a solid. Thus composition A containing 75% by weight of the filler is less viscous and easier to handle than is composition B. Alternatively, composition A is more able than composition B to be filled to 80% by weight or even higher of the filler, the increase resulting in improved abrasion resistance and improved hardness in fillings derived from the compositions.

EXAMPLE 25

52.4 g. (0.2 mole) of 4,4'-dicyclohexylmethane diisocyanate were placed in a flask together with 30 ml of dry methylene chloride, under nitrogen gas. 35.2 g. (0.1 mole) of oxypropylated Bisphenol-A were dissolved in 50 ml of dry methylene chloride and the solution was washed with 20 ml aliquots of dry methylene chloride into a dropping funnel. 10 drops of dibutyl tin dialurate (Mellite 12) were added to the solution in the dropping funnel.

The mixture in the flask was heated until the methylene chloride was refluxing gently and then the solution from the dropping funnel was added dropwise over a period of about 1 hours, with stirring. Stirring was continued for about 1½ hours after which time 26 g (0.2 mole) of hydroxyethyl methacrylate and 10 drops of dibutyl tin dialurate (Mellite 12) were added through the dropping funnel over a period of 15 minutes. The mixture was stirred for a further 3 hours and then was allowed to stand for about 70 hours. Infra-red spectra analysis of the mixture showed remaining face isocyanate and the mixture was allowed to stand for a further 48 hours. The resulting polymerisable prepolymer was isolated as a solid by treatment of the mixture with petroleum ether followed by removal of residual solvent in a rotary evaporator.

A dental filling composition was prepared from this solid prepolymer as described, and to the formulation described, in Example 24. Samples were cured as also is described in Example 24.

The prepolymer paste had good flow properties and the cured material was very translucent. Depth of cure achieved in 1 minutes was 6.1 mm, and after immersion in water for 24 hours at 37° C (Example 24), the cured material had compressive strength (average) of 264.2 N/mm$^2$ and a tensile strength (average) of 41.7 N/mm$^2$.

EXAMPLE 26

A dental filling material was prepared, formulated and cured as described in Example 25 except that 34.8 g (0.2 mole) of 2,4-toluene diisocyanate were used instead of the dicyclohexylmethane diisocyanate. The formulated paste had good flow properties and the cured material was translucent. Depth of cure in 1 minute was 5.5 mms. After immersion in water at 37° C for 24 hours, the material had a compressive strength (average) of 290.65 N/mm$^2$ and a tensile strength (average) of 47.6 N/mm$^2$.

What we claim is:
1. A dental filling composition comprising
    (a) from 60 to 80% by weight of the composition of an inorganic particulate filler selected from glass, quartz of silica of which at least 50% of the particles have a maximum dimension of not greater than 300 microns, and
    (b) a polymerisable material comprising:
        a polymerisable prepolymer being the reaction product of a urethane prepolymer and 2-hydroxyethyl methacrylate; the said urethane prepolymer being the reaction product of a di-isocyanate selected from the group consisting of 4,4'-diisocyanatodiphenylmethane, hexamethylene di-isocyanate, 4,4'-dicyclohexylmethane di-isocyanate and 2,4-tolylene di-isocyanate, and a diol being the condensate obtained by reacting 2,2-bis-(p-hydroxyphenyl)propane and propylene oxide in a molar ratio of 1:2;
        up to 100% by weight of the polymerisable prepolymer of methacrylic acid or an ester of methacrylic acid selected from the group consisting of methyl methacrylate, ethylene glycol dimethacrylate, hydroxyethyl methacrylate, triethylene glycol dimethacrylate and allyl methacrylate;
        and from 0.01 to 10% by weight of the polymerisable material of a photosensitive catalyst comprising a photosensitiser selected from the group consisting of fluorenone, benzil, camphorquinone and α-naphthil, and a reducing agent being dimethylaminoethyl methacrylate.

* * * * *